US010759076B2

(12) United States Patent
Grader et al.

(10) Patent No.: US 10,759,076 B2
(45) Date of Patent: Sep. 1, 2020

(54) DEVICE FOR THE MANUFACTURE OF PHARMACEUTICAL PATCHES

(71) Applicant: Luye Pharma AG, Miesbach (DE)

(72) Inventors: Ludwig Grader, Andernach (DE); Holger Piotrowski, Schliersee (DE)

(73) Assignee: Luye Pharma AG, Miesbach (DE)

( * ) Notice: Subject to any disclaimer, the term of this patent is extended or adjusted under 35 U.S.C. 154(b) by 121 days.

(21) Appl. No.: 15/322,902

(22) PCT Filed: Jul. 1, 2015

(86) PCT No.: PCT/EP2015/064996
§ 371 (c)(1),
(2) Date: Dec. 29, 2016

(87) PCT Pub. No.: WO2016/001312
PCT Pub. Date: Jan. 7, 2016

(65) Prior Publication Data
US 2017/0136648 A1  May 18, 2017

(30) Foreign Application Priority Data
Jul. 4, 2014  (EP) .................................... 14175754

(51) Int. Cl.
| B26D 7/18 | (2006.01) |
| B26F 1/38 | (2006.01) |
| A61K 9/70 | (2006.01) |
| A61F 13/02 | (2006.01) |

(52) U.S. Cl.
CPC ........ *B26D 7/1818* (2013.01); *A61F 13/0276* (2013.01); *A61K 9/7023* (2013.01); *B26D 7/18* (2013.01); *B26F 1/38* (2013.01); *A61F 2013/0296* (2013.01)

(58) Field of Classification Search
CPC ...... B26D 7/18; B26D 7/1836; B26D 7/1818; Y10T 83/2072; Y10T 83/2074; Y10T 83/2079; Y10T 83/2087
See application file for complete search history.

(56) References Cited

U.S. PATENT DOCUMENTS 2,789,640 A * 4/1957 Belden ................ B26D 7/1827
  156/256
3,626,561 A  12/1971 Luce et al.
(Continued)

FOREIGN PATENT DOCUMENTS

| CA | 2 373 276 A1 | 12/2000 | |
| GB | 1212409 A | * 11/1970 | ............. A43D 27/00 |

(Continued)

OTHER PUBLICATIONS

PCT/EP2015/064996—International Search Report, dated Sep. 15, 2015.
(Continued)

*Primary Examiner* — Jennifer B Swinney
(74) *Attorney, Agent, or Firm* — Curatolo Sidoti Co., LPA; Salvatore A. Sidoti; Floyd Trillis, III (57) ABSTRACT

The present invention relates to a device for the manufacture of pharmaceutical patches, a method for the manufacture of pharmaceutical patches, and a package comprising a pharmaceutical patch obtainable by said method.

16 Claims, 5 Drawing Sheets

(56) References Cited

U.S. PATENT DOCUMENTS

| | | | |
|---|---|---|---|
| 4,273,606 A * | 6/1981 | Trilli | B31D 1/021 |
| | | | 156/388 |
| 4,664,736 A | 5/1987 | Faasse, Jr. | |
| 4,836,070 A * | 6/1989 | Spano | B26D 7/0625 |
| | | | 83/104 |
| 4,841,712 A * | 6/1989 | Roou | B65B 9/02 |
| | | | 156/248 |
| 5,101,747 A * | 4/1992 | Gerber | B26D 7/1818 |
| | | | 112/470.13 |
| 5,197,938 A | 3/1993 | Chmielewski | |
| 5,470,004 A * | 11/1995 | Mineki | B26D 7/18 |
| | | | 225/103 |
| 6,365,178 B1 | 4/2002 | Venkateshwaran et al. | |
| 6,555,130 B2 | 4/2003 | Wüstling et al. | |
| 6,797,103 B2 * | 9/2004 | Mikkelsen | B08B 7/0028 |
| | | | 156/247 |
| 8,864,727 B2 | 10/2014 | Lee | |
| 2009/0155438 A1 | 6/2009 | Finkowski | |
| 2010/0320060 A1 | 12/2010 | Finkowski | |
| 2011/0020426 A1 | 1/2011 | Baird et al. | |
| 2011/0066120 A1 | 3/2011 | Lee | |

FOREIGN PATENT DOCUMENTS

| | | |
|---|---|---|
| WO | WO 96/40087 | 12/1996 |
| WO | WO 2011/034323 A2 | 3/2011 |

OTHER PUBLICATIONS

PCT/EP2015/064996—International Written Opinion, dated Sep. 15, 2015.

\* cited by examiner

DEVICE FOR THE MANUFACTURE OF PHARMACEUTICAL PATCHES

CROSS REFERENCE TO RELATED APPLICATIONS

This application is a national stage application of International Application No. PCT/EP2015/064996, filed 1 Jul. 2015, which claims priority from European Patent Application No. 14175754.2, filed 4 Jul. 2014, which applications are incorporated herein by reference.

The present invention relates to a device for the manufacture of pharmaceutical patches, a method for the manufacture of pharmaceutical patches, and a package comprising a pharmaceutical patch obtainable by said method.

The delivery of drugs through the skin provides many advantages. Primarily, it is a comfortable, convenient and non-invasive way of administering drugs. Moreover, such a means of delivery provides for uninterrupted therapy and a higher degree of control over drug concentrations in the blood.

Transdermal delivery of various active pharmaceutical ingredients (API) and pressure-sensitive adhesive matrix patches for transdermal delivery of such APIs are well known in the art of drug delivery. These matrix patches include a pressure-sensitive adhesive layer for affixing the patch to the skin and for carrying the API and any excipients that are directly incorporated into this adhesive layer. These adhesive matrix patches also typically include an inert backing layer, and a release liner which covers and protects the adhesive. The release liner is peeled off and discarded before applying the patch to the skin.

Numerous compositions which may be used for example as pressure-sensitive adhesive matrix materials in the preparation of pharmaceutical patches are described in the art (see for example WO 96/40087, U.S. Pat. No. 6,555,130 and WO 2011/034323).

A common problem associated with such matrix materials is the so-called "cold flow". Cold flow of an adhesive is the continuing dimensional change, which is due to inherent physicochemical properties of the polymer. Flowing of the adhesive material from the outer boundaries of a patch causes difficulties in removing the patch from the storage pouch because the patch may adhere to the pouch material (US 2011/0020426).

To overcome problems associated with the cold flow of adhesives, WO 96/40087 suggests crosslinking polyacrylate adhesives in order to increase their cohesive strength and resistance to cold flow.

CA 2,373,276 suggests a patch having a release liner which is divided by an incision for better peeling. To increase storage stability by avoiding leakage of pressure-sensitive adhesive from the patch by cold flow, the release liner is configured with two sections which overlap each other in the region where they are joined (cf. attached FIG. 1).

Methods for manufacturing pharmaceutical patches are also well known in the art and described, for example, in U.S. Pat. Nos. 6,365,178, 6,555,130 and US 2011/0020426. These methods generally comprise the steps of forming a laminate of the desired layers of the patch. In a continuous process this laminate can for example form a continuous sheet which is then punched to form the patches and a scrap web around the patches. The scrap web has to be removed before the patches can be further processed. Removal of the scrap web can, for example, be achieved by pulling the scrap web off so that only the patches remain for example on a supporting sheet.

A problem in the manufacturing of pharmaceutical patches is that sometimes the patches stick to the scrap web and therefore are removed together with the scrap web when this is pulled off. Patches sticking to the scrap web will be discharged together with the scrap web thereby losing products and in particular potentially expensive API.

Sticking of the patches to the scrap web is facilitated by the above described cold flow of for example the adhesive matrix material in one of the layers of the patches. Cold flow of these materials immediately starts after punching leading to a potential adhering of the punched patches to the scrap web.

The present invention deals with the problems associated with the cold flow of the adhesive materials being present in pharmaceutical patches. In particular, the present invention deals with the problem of the sticking of patches to the scrap web during their manufacture and the cost associated with the undesired discharge of patches together with the scrap web when this is pulled off. In a further embodiment the present invention also deals with the problem of potential leakage of pharmaceutical patches due to cold flow during storage and the undesired adhering of such patches to their packages.

To overcome the above described first problem of the sticking of punched patches to the scrap web during manufacture the present inventors have developed a device for the manufacture of pharmaceutical patches comprising a novel roller being equipped with hold-down devices to hold down the patches while the scrap web is pulled off.

The present invention therefore relates to a device for the manufacture of pharmaceutical patches comprising a) means for providing, such as continuously feeding a sheet of patch material, b) means for punching the sheet of patch material to form patches and a scrap web, and c) a roller at which the scrap web is pulled off, characterized in that the roller is equipped with one or more hold-down devices to hold down the patches that are being separated from the scrap web by pulling off the scrap web.

Figure 1:
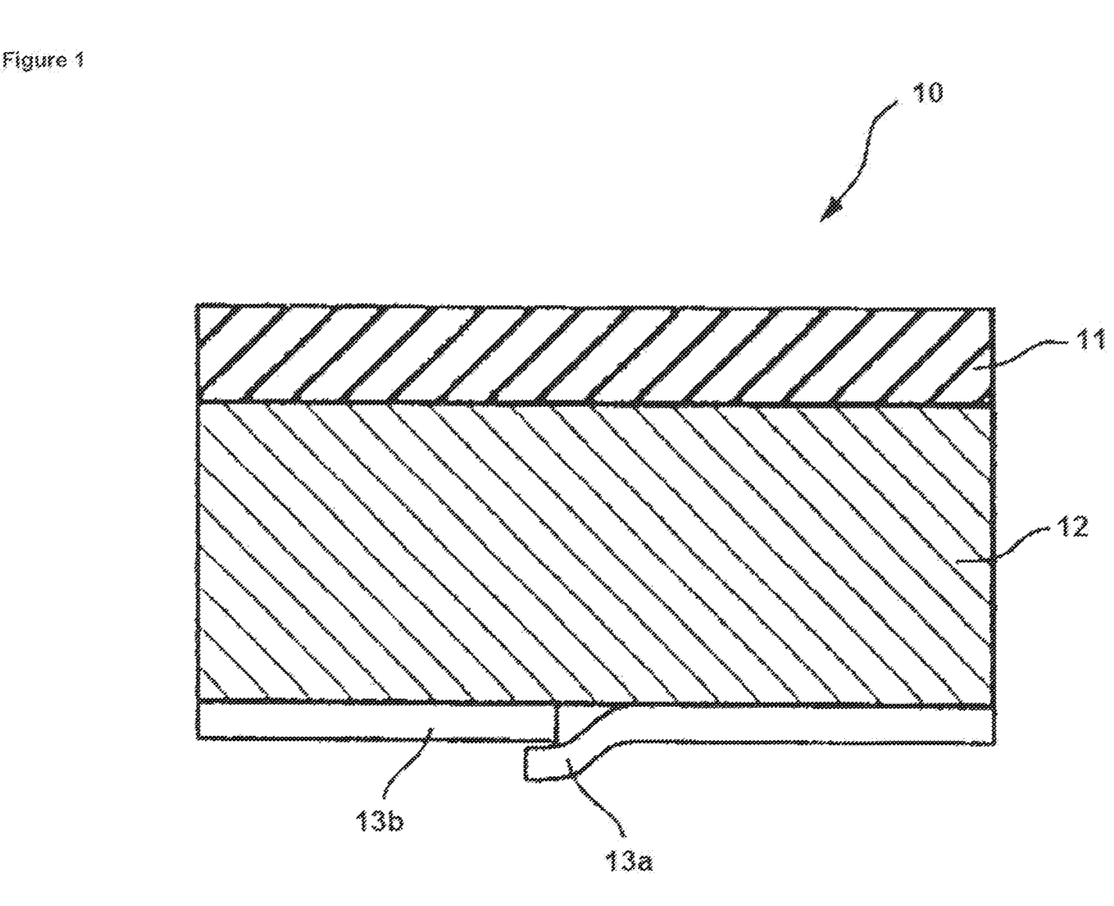

Pharmaceutical patches which can be manufactured with the device according to the invention comprise one or more layers. As shown in FIG. 1 a pharmaceutical patch 10 usually comprises at least three layers, namely a carrier layer 12 for carrying the API, a backing layer 11 which covers the carrier layer and which may be impermeable for the API and a release liner 13. The release liner is a disposable element which serves only to protect the device prior to application. Typically, the release liner is formed from a material impermeable to the drug, vehicle and adhesive, and which is easily stripped from the contact adhesive. As shown in FIG. 1, the release liner may be divided into two sections 13a and 13b by an incision and the two parts of the release liner may overlap each other in the region where they are joined in order to facilitate removal of the release liner prior to use of the patch and in order to reduce cold flow of the material in the above layer through the incision during storage.

The carrier layer 12 may be in the form of a matrix layer, such as a pressure-sensitive adhesive matrix layer comprising the API. In such case, the release of the API can be controlled by the composition of the carrier layer. Suitable materials are known to the person skilled in the art and disclosed for example in U.S. Pat. No. 6,555,130 and US 2011/0020426.

Figure 2:
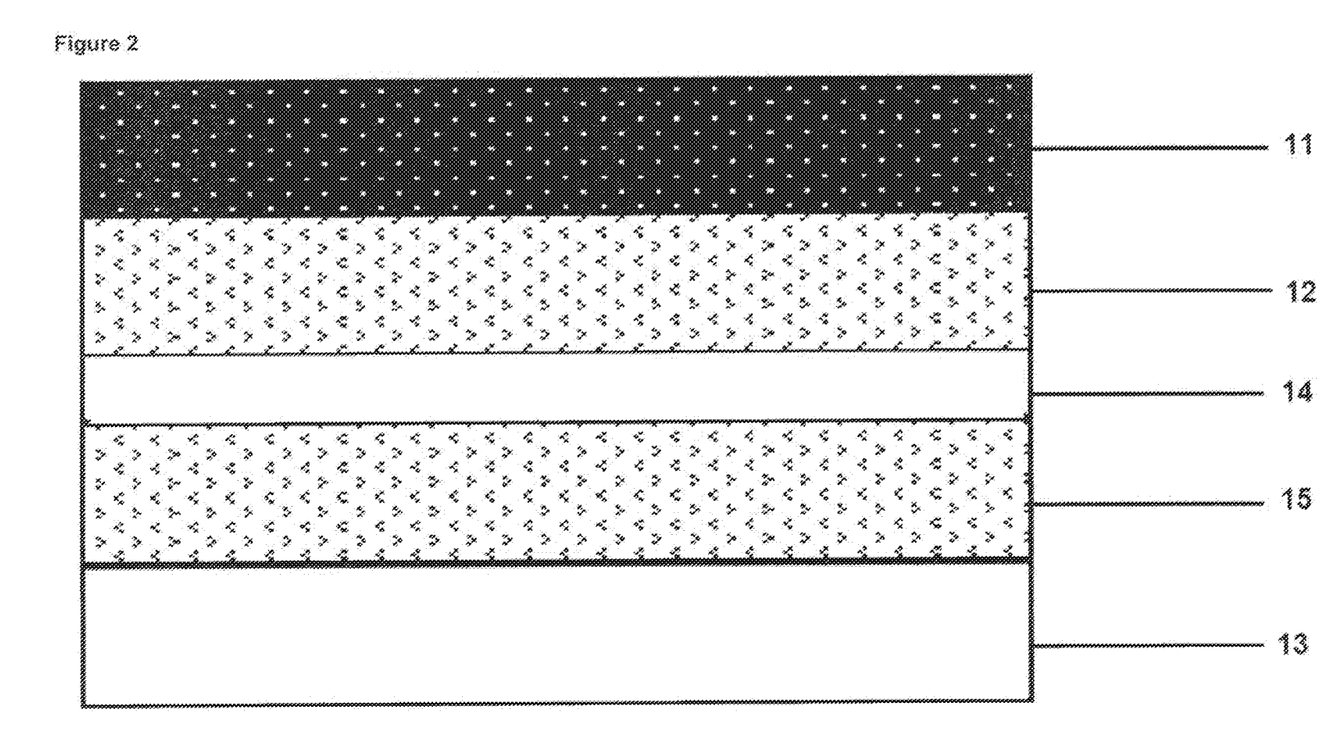

The pharmaceutical patch may comprise further layers, such as a membrane layer 14 below the carrier layer 12 and a skin-contact layer 15 being located between the membrane layer 14 and the release liner 13 (see FIG. 2). Thus, a membrane layer 14, if included, is typically located between the skin-contact layer 15 and the carrier layer 12 (the skin-contact layer being adjacent to the release liner 13 and the carrier layer being adjacent to the backing layer 11).

The membrane layer 14 may serve a variety of purposes, such as controlling the fusion and providing controlled release of the API. The membrane layer can be selected such that it is rate controlling, i.e. the presence of the membrane layer in the patch may change the skin penetration profile of the patch compared to a like patch not having the membrane.

Suitable membranes include continuous film membranes and microporous membranes. The membrane is preferably made of a polymeric material used conventionally by those skilled in the art. Polymer films which may be used for making the membrane layer include, without limitation, those comprising low density polyethylene, high density polyethylene, ethylene vinyl acetate copolymers, polypropylene and other suitable polymers.

The skin-contact layer 15 adjacent to the membrane layer 14 comprises an adhesive. The adhesive may be selected from silicons, natural and synthetic rubbers, polyisobutylene, neoprens, polybutadiens, polyisoprens, polysiloxans, acrylic adhesives including cross-linked and uncross-linked acrylic copolymers, vinylacetate adhesives, polyacrylates, ethylene vinylacetate copolymers, styrene-isoprene copolymers, polyurethanes, plasticized polyether block amide copolymers, plasticized styrene-rubber block copolymers, and mixtures thereof.

The various layers of patch material may have any appropriate thickness.

As known to the skilled person and as described for example in U.S. Pat. No. 6,555,130 and US 2011/0020426 the desired layers forming for example the release liner, the skin-contact layer, the membrane layer, the carrier layer and the backing layer may be produced for example by casting a liquid mass comprising the mixed components of the carrier layer onto a continuous sheet of release liner, evaporating the corresponding solvent in a drying step and laminating the thus obtained sheet with the backing layer. Other layers may be included within the laminate as required.

The laminate may be formed on a separate continuous support sheet or for example the release liner or the backing layer of the patch may serve as support sheet.

In the context of the present invention the term "sheet of patch material" defines one or more of the above described layers. Thus, the sheet of patch material may be a laminate of several layers, such as a laminate of a release liner, a carrier layer and a backing layer. The laminate may comprise additional layers as described above and exemplified in FIG. 2. In these cases, the "sheet of patch material" may comprise all layers of the final patch. However, the term "sheet of patch material" also covers embodiments where said sheet consists of only a single layer or two or more layers but not all layers of the final patch. In this case, the sheet of patch material is suitable for forming an intermediate product which can then be processed into the final patch by adding additional layers as required.

From the sheet of patch material patches having a predetermined shape and size are punched using a usual punching device well-known to the person skilled in the art. This device punches the layer(s) of patch material forming the sheet thereby defining areas having the shape and size of the patches to be manufactured and areas between the patches. The areas between the patches usually form a continuous scrap web which is pulled off over a deflection device thereby separating the patches from the scrap web. The thus obtained patches are either final products or intermediates which may be further processed into final products.

As explained above, some of the patches usually stick to the scrap web and therefore are removed together with the scrap web thereby resulting in loss of patches and in particular of potentially expensive API.

In order to avoid loss of patches by sticking to the scrap web, the device according to the present invention comprises a roller as deflection device, wherein said roller is equipped with one or more hold-down devices to hold down the patches that are being separated from the scarp web by pulling off the scrap web.

In one embodiment, said roller is a non-rotary roller, i.e. the roller is a static deflection device, preferably in the shape of a cylinder. However, in a preferred embodiment, said roller is a rotary roller, i.e. is rotating when the patches are being separated from the scrap web.

Figure 3A:
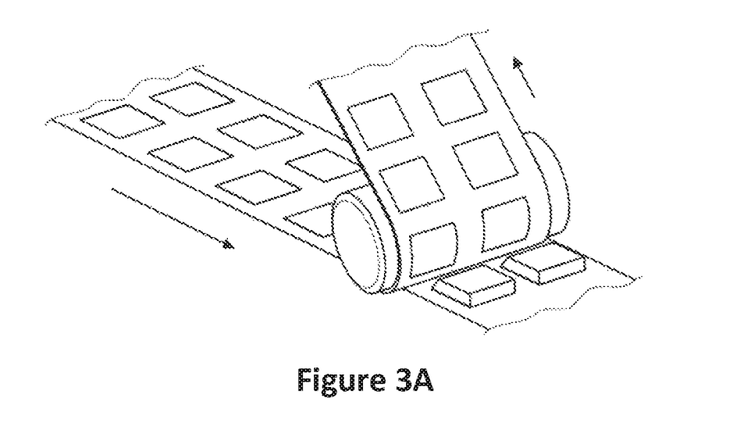
Figure 3B:
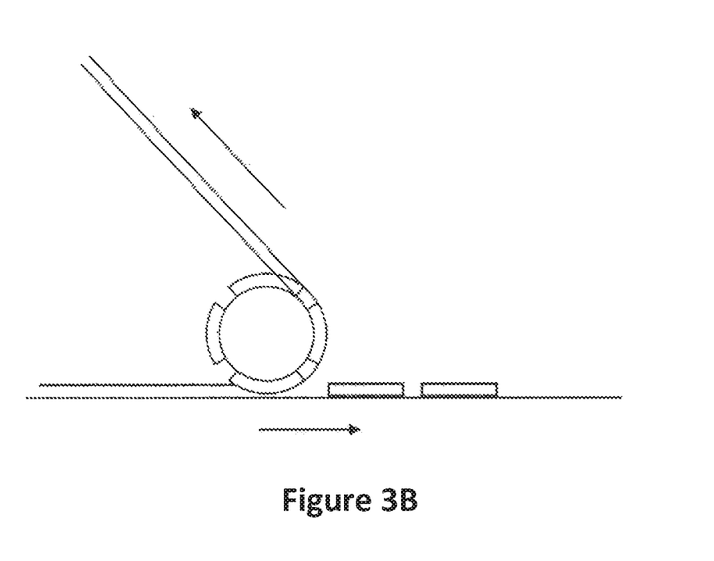
Figure 4:
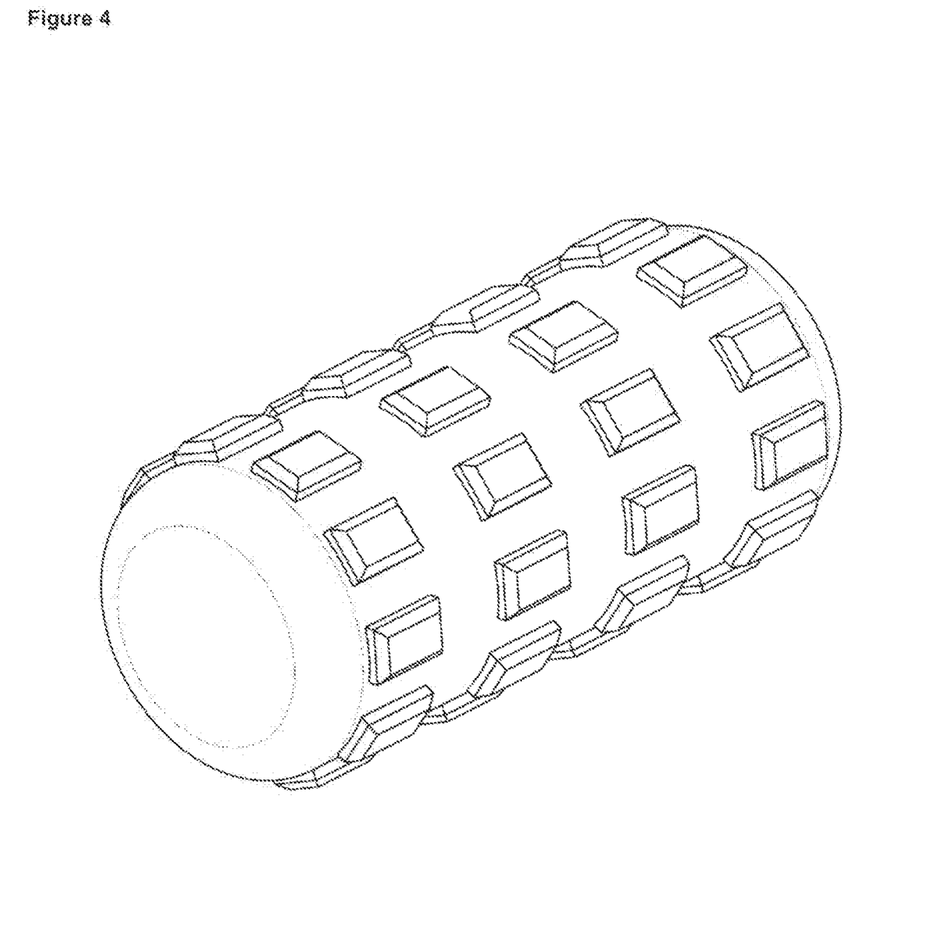

The step of pulling off the scrap web using a roller is schematically shown in FIGS. 3A and 3B. FIG. 3A is a partial perspective front side view of the step of pulling off the scrap web using a roller, and FIG. 3B is a side view of the same step. One embodiment of a roller according to the invention being equipped with hold-down devices is shown in FIG. 4. Another embodiment of a suitable roller is shown in FIG. 5.

As shown in FIGS. 3 and 4, the roller in the device according to the invention is equipped with hold-down devices which are located on the surface of the roller such that they hold down the patches while the scrap web is pulled off. Thus, the number of hold-down devices on the roller is not particularly limited but in one embodiment, as schematically shown in FIG. 4, the roller is equipped with a number of hold-down devices being sufficient such that each one hold-down device interacts with one patch while the scrap web can be freely pulled off between the hold-down devices. Thus, if for example the sheet of patch material is punched such that perpendicularly to the feeding direction four patches are formed parallel to each other, then the roller should also be equipped with four hold-down devices located side by side in axial direction of the roller. Circumferentially the number of hold-down devices on the roller should be equivalent to the number of patches with which the roller engages during one revolution.

Figure 5:
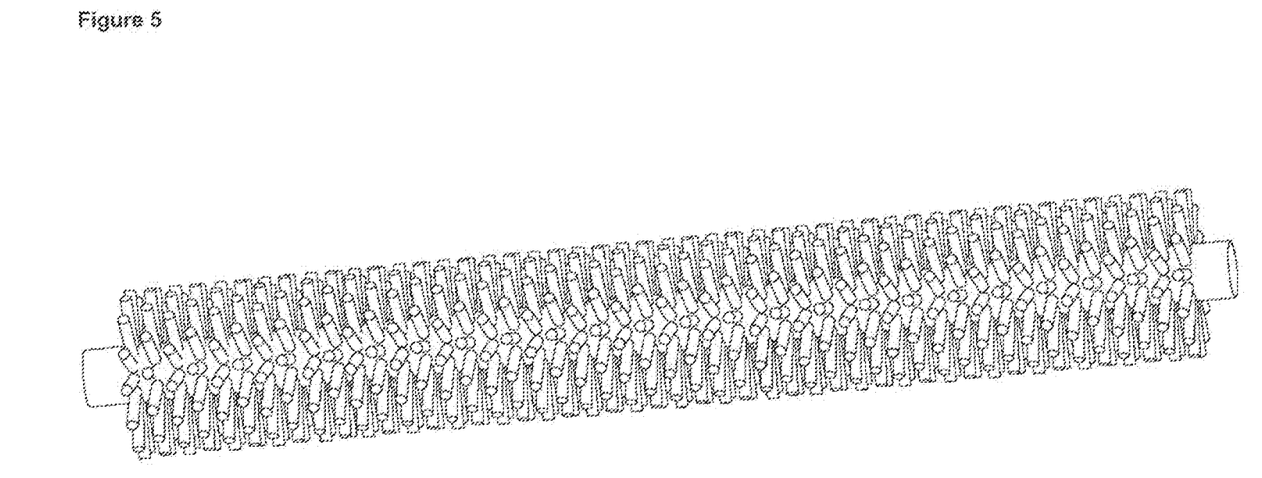

In another embodiment, as schematically shown in FIG. 5, the roller is a brush roller having elastic, flexible and/or deformable bristles. The surface of said brush roller might be fully covered with bristles, might have one or multiple lines of bristles or might have selected areas covered with bristles.

In one embodiment the roller is equipped with at least 2, preferably at least 4, 6, 8, 10, 12, 14, 16, 18, 20, 22, 24, 26, 28, 30, 32, 34, 36, 38 or 40 hold-down devices. Preferably all hold-down devices on one roller are identical. Furthermore, the roller preferably has at least two symmetry planes, more preferably at least four symmetry planes.

The size and three-dimensional shape of the hold-down devices is not particularly limited. Furthermore, the roller may be equipped with two or more different types of hold-down devices, although it is preferred that all hold-down devices on a roller have the same size and three-dimensional shape.

One relevant feature can be the size of the hold-down devices' area which contacts the patch when holding it down while the scrap web is pulled off. This size is defined as the size of the area which contacts a patch while the hold-down device holds down the patch when pulling off the scrap web. Furthermore, this area is defined as the total area of all hold-down devices simultaneously interacting with one patch while holding down the patch when the scrap web is pulled off. The size of this area is not particularly limited but should be equal to or smaller than the surface area of the patch to be contacted. If the surface area of the hold-down device is larger than the surface area of the patch to be contacted there is a risk that a single hold-down device also interacts with the scrap web thereby preventing the scrap web from being pulled off or damaging the scrap web so that it might tear thereby interrupting the manufacturing process. On the other hand, if this surface area is small, the pressure exerted by the hold-down device(s) on the patch can be high. Therefore, the ratio of the surface area of the hold-down device(s) for contacting one patch to the surface area of this patch may for example be equal to or greater than 1:10, preferably equal to or greater than 1:4 and most preferably equal to or greater than 1:2.

Typically, the size of a pharmaceutical patch ranges from 2 $cm^2$ to 60 $cm^2$, preferably from 2 $cm^2$ to 50 $cm^2$, more preferably from 2 $cm^2$ to 40 $cm^2$, even more preferably from 3 $cm^2$ to 30 $cm^2$. Thus, the surface area of the hold-down devices for contacting the patches may be within these ranges or smaller. However, since pharmaceutical patches may also be smaller or larger, the surface area of the hold-down devices for contacting the patches is not particularly limited and may be selected by the skilled person according to the requirements and in particular according to the size of the pharmaceutical patch to be produced.

It is self-evident to the skilled person that not only the surface area of the hold-down device(s) for contacting one patch should not be larger than the surface area of this patch but also the hold-down device should be attached to the roller at a position such that the surface for contacting the patch only contacts the area of the patch but not the area of the scrap web.

The three-dimensional shape and material of the hold-down devices can be selected by the skilled person according to their function to hold down the patches while the scrap web is pulled off. For example, the hold-down device can be in the form of a single plug or in the form of a plurality of small plugs or burls. If the hold-down device is not a single plug but a plurality of small plugs or burls, the surface area of the hold-down device for contacting one patch is calculated as the sum of the surface areas of all small plugs or burls contacting the one patch.

Thus, in the context of the present invention, the term "hold-down device" is to be understood as any means suitable for holding down the patches that are being separated from the scrap web by pulling off the scrap web. Any element projecting from the surface of the roller can be suitable for this purpose. As described above, such element can be a single plug or can be divided into several elements, such as a plurality of plugs or burls. The term "burl" defines an element, such as a pin, gudgeon or bristle (like a bristle of a brush).

A plurality of such burls together may form one hold-down device. If the roller is a brush roller being partially or fully covered with bristles, it is possible or even unavoidable that one or more bristles will contact the scrap web. The present inventors, however, found that, if the bristles are sufficiently flexible and/or deformable, the force of the scrap web exerted to the bristles when the scrap web is pulled off is sufficient to deform the bristles in a manner sufficient for allowing the scrap web to be pulled off, for example by pressing the bristles against the roller. At those areas where the bristles interact with the patches, the force exerted on the bristles is lower compared to those areas where the bristles interact with the scrap web and, therefore, those bristles which act as hold-down device are able to effectively hold-down the patches while those bristles which interact with the scrap web are deformed by the higher force exerted by the scrap web so that they do not adversely affect the process of pulling off the scrap web from the patches. When the scrap web is removed from the roller, the pressure exerted by the scrap web on the bristles is released and the elasticity of the bristles should be such that they take their original shape. Thus, the bristles should be sufficiently flexible and/or deformable in order to be deformed by the scrap web when being pulled off, thereby allowing the pulling off of the scrap web but at the same time should have sufficient stiffness in order to effectively hold down the patches while the scrap web is pulled off. At the same time, the bristles should be sufficiently elastic in order to take their original shape when the pressure exerted by the scrap web subsides. The same result can be achieved by for example spring-mounting the bristles, or other burls.

The material of the hold-down devices is not particularly limited and can be, for example, the same material as the surface of the roller.

In a preferred embodiment the hold-down devices are elastic, flexible and/or deformable. In this case, either the hold-down device in itself can be elastic, flexible and/or deformable, for example by using an elastic, flexible and/or deformable material for providing the plug, plugs or burls, or the hold-down device can be mounted to the roller in an elastic, flexible and/or deformable manner, such as spring-mounted. Also combinations of plugs or burls being formed of a, elastic, flexible and/or deformable material and an elastic, flexible and/or deformable mounting of the hold-down device to the roller are possible. In this context "spring-mounted" is understood to encompass any kind of spring including for example hydraulic springs and air springs.

For holding down the patches while the scrap web is pulled off, the hold-down devices must exert a certain pressure to the patch. In order to avoid possible damages it is preferred that the hold-down device applies a maximum pressure of 1.000 $kN/m^2$ to the patch, preferably a maximum pressure of 750 $kN/m^2$, 500 $kN/m^2$, 250 $kN/m^2$, 100 $kN/m^2$, 75 $kN/m^2$, 50 $kN/m^2$, 25 $kN/m^2$, 10 $kN/m^2$, 5 $kN/m^2$ or 1 $kN/m^2$.

In a preferred embodiment the hold-down device applies pressure to the patch being sufficiently low to not deform the patch. The maximum pressure which may be applied to the patch without deforming it depends on the composition of the sheet of patch material and can be determined by the skilled person according to the specific requirements.

On the other hand, the present inventors surprisingly found that, if a certain pressure is applied by the hold-down device to the patch, it is possible to deform, in particular permanently deform the patch. It was found that, if the pressure applied by the hold-down device to the patch is high enough, a recessed area in the surface of the patch is formed. This recessed area has substantially the same shape as the surface of the hold-down device contacting the patch. Furthermore, the depth of the recessed area depends on the pressure exerted by the hold-down device to the patch while contacting it.

A recessed area can be obtained in one surface of the patch if the hold-down device exerts pressure on the one side of the patch while the opposite side of the patch is supported by a flat surface. Alternatively, the patch may be supported on a surface comprising a convexity basically opposite to the area where the hold-down device contacts the patch. In this case, the patch can be provided with recessed areas on opposite sides.

The present invention in a further embodiment therefore relates to the above described device for the manufacture of pharmaceutical patches wherein the hold-down device applies a pressure to the patch being sufficient to deform the patch, in particular to permanently deform the patch on one of its sides or on opposite sides.

It was found that recessed areas in one or opposite surfaces of a patch facilitate removing the patch from a package, in particular when the package is a pouch. The recessed areas allow an easier grasping of the patch by providing more space between the patch and the walls of the pouch. This results in an increased patient compliance.

Additionally, if the release liner of the patch is divided by an incision for better peeling but the two sections of the release liner are not overlapping each other, there is a risk that for example pressure-sensitive adhesive may leak through the slit between the two sections of the release liner by cold flow. In this case, the patch tends to stick to the package which can make removal of the patch from the package difficult. In this case, the recessed area can be provided on the side of the release liner and in the area of the slit between the two sections of the release liner. If during storage pressure-sensitive adhesive leaks through the slit, it will leak into the recessed area which in turn results in less sticking of the patch to the package wall.

In a further embodiment the present invention relates to the use of the above described roller in the manufacture of pharmaceutical patches. In this embodiment the above described preferred embodiments of the roller and its hold-down devices also apply.

Furthermore, the invention relates to a method for the manufacture of pharmaceutical patches comprising the steps of a) punching a sheet of patch material to form the patches and a scrap web, and b) separating the patches from the scrap web by pulling off the scrap web at a roller, characterized in that the patches being separated from the scrap web are held down by means of one or more hold-down devices on the roller while the scrap web is pulled off.

In one preferred embodiment of this method the pressure applied to the patches by the hold-down devices while pulling off the scrap web is sufficiently low to not deform the patches.

In another embodiment of this method, the pressure applied to the patches by the hold-down devices while pulling off the scrap web is sufficient to deform said patch. By deforming, in particular permanently deforming said patch, a recessed area is obtained on one side of the patch. As described above with respect to the device of the invention, also the method can be modified so as to obtain another recessed area on the opposite side of the patch.

Furthermore, if the pressure-sensitive adhesive in the sheet of patch material is covered by a slitted release liner, it was found to be advantageous if the hold-down device provides recessed areas in that way that the slit of the release liner is prevented from contact with the packaging material. This has the advantage that leakage of the pressure-sensitive adhesive through the slit is minimized.

Patches being deformed on one or both sides which are obtainable by the above method are also part of the present invention.

Finally, the present invention relates to a package comprising a pharmaceutical patch being deformed on one or both of its sides.

The invention claimed is:

1. A device for manufacturing pharmaceutical patches comprising
a device for providing a sheet of patch material on a support sheet,
a punching device for forming patches having a surface area and a scrap web, and
a roller at which the scrap web is pulled off,
wherein the roller is equipped with one or more hold-down devices to hold down the patches on the support sheet such that the patches are being separated from the scrap web by pulling off the scrap web, wherein each hold-down device interacts with one patch, wherein each hold-down device is configured to hold down one patch while the scrap web can be freely pulled off between the one or more hold-down devices, and wherein the one or more hold-down devices do not contact the scrap web.

2. The device of claim 1, wherein each hold-down device has a surface area for contacting the patch, wherein the surface area is equal to or smaller than the surface area of the patch to be contacted.

3. The device of claim 1, wherein the ratio of the surface area of the hold-down device(s) to the surface area of the patch is equal to or greater than 1:10.

4. The device of claim 1, wherein the hold-down device comprises a plurality of burls.

5. The device of claim 4, wherein the roller is a brush roller and the plurality of burls are elastic, flexible and/or deformable bristles.

6. The device of claim 1, wherein the hold-down device is elastic, flexible and/or deformable, and/or the hold-down device is spring mounted.

7. The device of claim 1, wherein the hold-down device applies a maximum pressure of 1000 kN/m$^2$ to the patch.

8. The device of claim 1, wherein the hold-down device applies a pressure to the patch being sufficiently low to not deform the patch.

9. The device of claim 1, wherein the roller is equipped with at least two hold-down devices.

10. The device of claim 9, wherein the hold-down devices are identical.

11. The device of claim 9, wherein the roller has at least two symmetry planes.

12. The device of claim 1, wherein the ratio of the surface area of the hold-down device(s) to the surface area of the patch is equal to or greater than 1:4.

13. The device of claim 1, wherein the ratio of the surface area of the hold-down device(s) to the surface area of the patch is equal to or greater than 1:2.

14. A method comprising utilizing a roller being equipped with one or more hold-down devices in manufacturing pharmaceutical patches, wherein each hold-down device interacts with one patch, wherein each hold-down device is configured to hold down one patch while the scrap web can be freely pulled off between the one or more hold-down devices, and wherein the one or more hold-down devices do not contact the scrap web.

15. A method for the manufacture of pharmaceutical patches comprising
punching a sheet of patch material to form the patches and a scrap web on a sheet support, and
separating the patches from the scrap web by pulling off the scrap web at a roller, wherein the patches being separated from the scrap web are held down on the sheet support by means of one or more hold-down devices on the roller while the scrap web is pulled off, wherein each hold-down device interacts with one patch, wherein each hold-down device is configured to hold down one patch while the scrap web can be freely pulled off between the one or more hold-down devices, and wherein the one or more hold-down devices do not contact the scrap web.

16. The method of claim 15, wherein a pressure applied to the patches by the hold-down devices while pulling off the scrap web is sufficiently low to not deform the patches.

\* \* \* \* \*